US010353959B2

(12) United States Patent
Morimoto

(10) Patent No.: US 10,353,959 B2
(45) Date of Patent: Jul. 16, 2019

(54) COMPONENT ASSEMBLY SYSTEM AND METHOD USING INSPECTION INFORMATION

(71) Applicant: FANUC CORPORATION, Yamanashi (JP)

(72) Inventor: Kenjirou Morimoto, Yamanashi (JP)

(73) Assignee: FANUC CORPORATION, Yamanashi (JP)

( * ) Notice: Subject to any disclaimer, the term of this patent is extended or adjusted under 35 U.S.C. 154(b) by 114 days.

(21) Appl. No.: 15/590,128

(22) Filed: May 9, 2017

(65) Prior Publication Data
US 2017/0329874 A1 Nov. 16, 2017

(30) Foreign Application Priority Data
May 13, 2016 (JP) ................................ 2016-097374

(51) Int. Cl.
*G06F 17/30* (2006.01)
*G06F 16/907* (2019.01)
(Continued)

(52) U.S. Cl.
CPC .............. *G06F 16/907* (2019.01); *G06F 7/16* (2013.01); *G06F 16/90328* (2019.01);
(Continued)

(58) Field of Classification Search
USPC .......................................................... 702/35
See application file for complete search history.

(56) References Cited

U.S. PATENT DOCUMENTS 4,332,012 A * 5/1982 Sekine .................. B62D 65/02
209/552
2006/0041371 A1* 2/2006 Baxter ................ F02D 41/2425
701/115
(Continued)

FOREIGN PATENT DOCUMENTS

CN 1414894 A 4/2003
CN 1526934 A 9/2004
(Continued)

*Primary Examiner* — Paul D Lee
(74) *Attorney, Agent, or Firm* — Hauptman Ham, LLP

(57) ABSTRACT

A component assembly system and method, by which an optimum combination of components can be determined by using inspection information of each component. The system has: an inspection information reading section for reading first and second inspection information regarding assembling of first and second components; a component reserving section for reserving each component; a storing section for storing a relationship between the inspection information of each component and a reserve position of each component; a grouping section for providing at least one first and second groups respectively including the first and second components; a combination determining section for determining a combination of the first and second components on one-to-one correspondence, by using the first and second inspection information; and a component conveying device for conveying the first and second components corresponding to the determined combination from the component reserving section to an assembly device, by using the stored relationship.

6 Claims, 4 Drawing Sheets

(51) Int. Cl.
- *G06F 16/9032* (2019.01)
- *G06F 16/903* (2019.01)
- *G06F 7/16* (2006.01)
- *G06Q 50/04* (2012.01)
- *B07C 5/34* (2006.01)
- *G01N 21/88* (2006.01)

(52) U.S. Cl.
CPC .. *G06F 16/90344* (2019.01); *G06F 16/90348* (2019.01); *G06Q 50/04* (2013.01); *B07C 5/34* (2013.01); *G01N 21/88* (2013.01); *G01N 2201/024* (2013.01); *Y02P 90/30* (2015.11)

(56) References Cited

U.S. PATENT DOCUMENTS

| | | | |
|---|---|---|---|
| 2008/0226122 A1* | 9/2008 | Thompson | G06K 9/20 382/100 |
| 2009/0030542 A1* | 1/2009 | Lindstrom | G05B 19/4189 700/113 |
| 2009/0259344 A1* | 10/2009 | Watson | G06Q 10/08 700/283 |
| 2010/0128389 A1* | 5/2010 | Chandrasekaran | G11B 25/043 360/98.08 |
| 2011/0307090 A1* | 12/2011 | Hamazoe | G06F 17/5086 700/104 |
| 2015/0081158 A1 | 3/2015 | Stilkerich | |
| 2016/0207578 A1* | 7/2016 | Perry | H04B 5/0062 |

FOREIGN PATENT DOCUMENTS

| | | | |
|---|---|---|---|
| JP | S52-140076 A | | 11/1977 |
| JP | H05113326 A | | 5/1993 |
| JP | 9-314431 A | | 12/1997 |
| JP | 2002-263969 A | | 9/2002 |
| JP | 2009-59220 A | | 3/2009 |
| JP | 2009059220 A | * | 3/2009 |
| JP | 2009-265983 A | | 11/2009 |

\* cited by examiner

COMPONENT ASSEMBLY SYSTEM AND METHOD USING INSPECTION INFORMATION

RELATED APPLICATIONS

The present application claims priority to Japanese Patent Application No. 2016-097374 filed May 13, 2016, the disclosure of which is hereby incorporated by reference herein in its entirety.

BACKGROUND OF THE INVENTION

1. Field of the Invention

The preset invention relates to a component assembly system and a component assembly method, for assembling a plurality of components.

2. Description of the Related Art

There are various well-known systems or methods for manufacturing a product by assembling a plurality of components. As a relevant prior art document, JP H09-314431 A discloses an automatic assembly/convey system for measuring, selecting, assembling and conveying two components configured to be fitted with each other, such as a valve adjuster and a body of a plunger.

Further, JP 2009-059220 A discloses a production management system used in a production method by which a plurality of components each having a fitting or fitted portion are manufactured, and then the fitting portion and the fitted portion of the manufactured components are assembled to each other so as to make a product.

In assembling components, a dimensional error of each component has an effect on the difficulty in assembling the components or on the quality of an assembled product. In automatic assembly equipment, whether or not the automatic assembly can be carried out depends on the difficulty in the assembling. In particular, when two components, which are difficult to assemble due to dimensional errors thereof, are selected as the components to be assembled, the operation of the automatic assembly equipment may be suspended. Further, the assembling of the components may be impossible due to an error which is unexpected when designing the equipment.

Even if dimensional errors of all given components are within a specified tolerance and a dimension of an assembled product is within a designed tolerance, the dimension of the product vary within the designed tolerance when the components are randomly combined. Therefore, it may be difficult to improve the quality (or dimensional accuracy) of the product.

In the technique of JP H09-314431 A, the dimension of each first component is measured, the first components are stocked while being classified by dimension, the dimension of a second component is measured, and one of the stocked first components is selected so that a fitting clearance between the second component and the selected first component is optimum. In this technique, however, some of the first components which do not form the optimum clearance relative to the second component may be stocked for a long time.

On the other hand, the technique of JP 2009-059220 A appears to be intended to rank components based on accuracy of finishing thereof, generate ranking data indicating whether or not prescribed portions of respective ranked components can be suitably combined with each other, and determine or manage combinations of each component based on the ranking data. In this technique, however, it is necessary to previously prepare or determine the rank as described above.

Further, in either of JP H09-314431 A or JP 2009-059220 A, a stocking place or the rank of each component is determined without depending on the other component. Therefore, when a plurality of groups of components is provided, it may be difficult to determine an optimum combination of the components between the groups.

SUMMARY OF THE INVENTION

Therefore, an object of the present invention is to provide a component assembly system and a component assembly method, by which an optimum combination of components can be determined by using inspection information of each component and by considering inspection of the same type of other components.

Accordingly, one aspect of the present invention provides a component assembly system, comprising: an inspection information reading section configured to read first inspection information regarding assembling, added to each of a plurality of first components each having a dimension within a specified tolerance, and second inspection information regarding assembling, added to each of a plurality of second components each having a dimension within a specified tolerance and being configured to be assembled to the first component; a component reserving section configured to reserve each of the first and second components; a storing section configured to store a relationship between each component, the inspection information of each component, and a reserve position of each component in the component reserving section; a grouping section configured to provide a first group including a predetermined number of the first components and a second group including the predetermined number of the second components; a combination determining section configured to determine a combination of the first component in the first group and the second component in the second group on one-to-one correspondence, by using the first inspection information of the first components in the first group and the second inspection information of the second components in the second group; and a component conveying device configured to convey the first and second components corresponding to the determined combination from the component reserving section to an assembly device, by using the relationship stored in the storing section.

The combination determining section may be configured to order the first components in the first group with respect to easiness of assembling by using the first inspection information, order the second components in the second group with respect to easiness of assembling by using the second inspection information, and determine the combination of the first and second components based on the ordering of the first components and the ordering of the second components so that dispersion of the easiness of assembling between each combination is minimized.

Alternatively, the combination determining section may be configured to order the first components in the first group with respect to a dimensional error of assembled first and second components, order the second components in the second group with respect to the dimensional error of the assembled first and second components, and determine the combination of the first and second components based on the ordering of the first components and the ordering of the second components so that dispersion of the dimensional error of the assembled first and second components between each combination is minimized.

Alternatively, the combination determining section may be configured to evaluate all of the combinations of the first components in the first group and the second components in the second group by using the first and second inspection information, and determine the combination of the first and second components based on the evaluation.

Another aspect of the present invention provides a component assembly method, comprising the steps of: reading first inspection information regarding assembling, added to each of a plurality of first components each having a dimension within a specified tolerance, and second inspection information regarding assembling, added to each of a plurality of second components each having a dimension within a specified tolerance and being configured to be assembled to the first component; reserving each of the first and second components in a component reserving section; storing a relationship between each component, the inspection information of each component, and a reserve position of each component in the component reserving section; providing a first group including a predetermined number of the first components and a second group including the predetermined number of the second components; determining a combination of the first component in the first group and the second component in the second group on one-to-one correspondence, by using the first inspection information of the first components in the first group and the second inspection information of the second components in the second group; and conveying the first and second components corresponding to the determined combination from the component reserving section to an assembly device, by using the stored relationship.

The step of determining may include ordering the first components in the first group with respect to easiness of assembling by using the first inspection information, ordering the second components in the second group with respect to easiness of assembling by using the second inspection information, and determining the combination of the first and second components based on the ordering of the first components and the ordering of the second components so that dispersion of the easiness of assembling between each combination is minimized.

Alternatively, the step of determining may include ordering the first components in the first group with respect to a dimensional error of assembled first and second components, ordering the second components in the second group with respect to the dimensional error of the assembled first and second components, and determining the combination of the first and second components based on the ordering of the first components and the ordering of the second components so that dispersion of the dimensional error of the assembled first and second components between each combination is minimized.

Alternatively, the step of determining may include evaluating all of the combinations of the first components in the first group and the second components in the second group by using the first and second inspection information, and determining the combination of the first and second components based on the evaluation.

BRIEF DESCRIPTION OF THE DRAWINGS

The above and other objects, features and advantages of the present invention will be made more apparent by the following description of the preferred embodiments thereof, with reference to the accompanying drawings, wherein.

DETAILED DESCRIPTIONS

Figure 1:
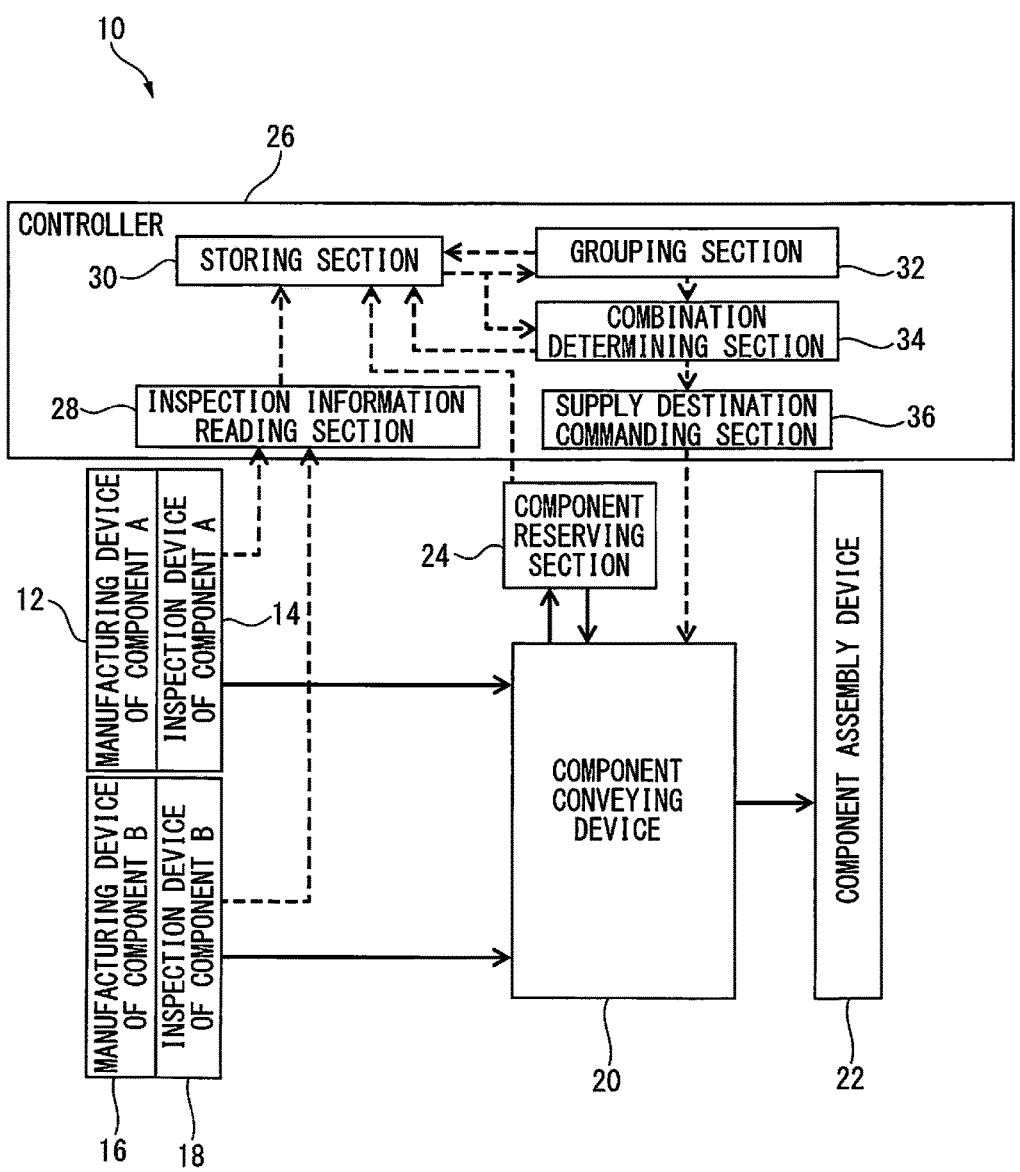
FIG. 1 is a functional block diagram of a component assembly system according to a preferred embodiment of the present invention.

FIG. 1 is a functional block diagram of a component assembly system 10 according to a preferred embodiment of the present invention. Component assembly system 10 includes: a first manufacturing device 12 such as a machine tool for manufacturing a first component A; a first inspection device 14 for inspecting (e.g., measuring a dimension of) component A manufactured by first manufacturing device 12; a second manufacturing device 16 such as a machine tool for manufacturing a second component B configured to be assembled to component A; a second inspection device 18 for inspecting (e.g., measuring a dimension of) component B manufactured by second manufacturing device 16; a component conveying device 20 such as a robot or a belt conveyor configured to convey component A inspected by first inspection device 14 and component B inspected by second inspection device 18; and a component assembly device 22 configured to assemble components A and B conveyed by component conveying device 20.

Further, component assembly system 10 includes: a component reserving section 24 such as a component shelf or a stocker configured to temporarily reserve the components conveyed by component conveying device 20 from first inspection device 14 or second inspection device 18; and a controller 26 configured to control a motion or operation of component conveying device 20. For example, controller 26 may be a personal computer or a server located away from component conveying device 20 or component assembly device 22. Controller 26 includes: an inspection information reading section 28 configured to read first inspection information regarding assembling, added to each of first components A each having a dimension within a specified tolerance, and second inspection information regarding assembling, added to each of second components B each having a dimension within a specified tolerance; a storing section 30 configured to store a relationship between each component, the inspection information of each component, and a reserve position of each component in component reserving section 24; a grouping section 32 configured to provide one or more first group each including a predetermined number (five in an example as described below) of first components A and one or more second group including the predetermined number (same as the number of first components A) of second components B; a combination determining section 34 configured to combine one first group and one second group, and determine a combination of the first component in the combined first group and the second component in the combined second group on one-to-one correspondence, by using the first inspection information of the first components in the combined first group and the second inspection information of the second components in the combined second group (i.e., the first and second components are combined without excess or shortage); and a supply destination commanding section 36 configured to transmit a command to component conveying device 20 in order that component conveying device 20 conveys the first and second components corresponding to the combination determined by combination determining section 34 from component reserving section 24 to assembly device 22. For example, the functions of inspection information reading section 28, storing section 30, grouping section 32, combination determining section 34 and supply destination commanding section 36 may be realized by a memory or a processor included in controller 26. In this regard, the expression "one-to-one correspondence" means that, between the first and second group including the same number of components, each component in the first group is combined (associated) with either of components in the second group, and the components in the first group are combined with respective different components in the second group. In other words, one component in one group cannot be combined with plural components in the other group.

Figure 2:
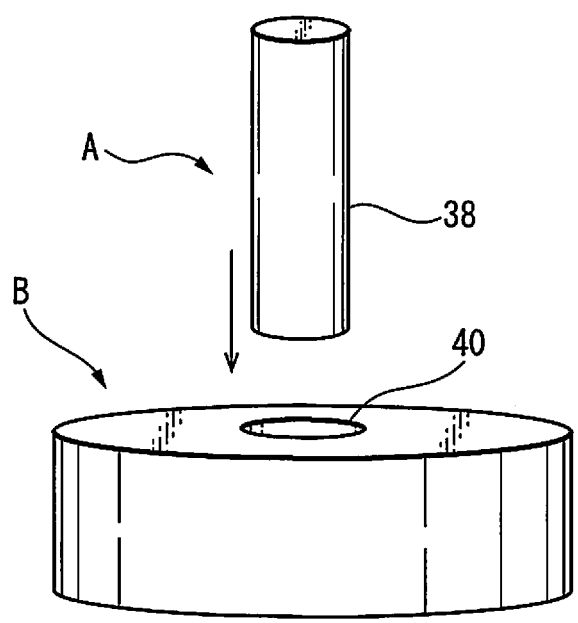
FIG. 2 is a view showing a concrete example of shapes of first and second components.

FIG. 2 shows a concrete example of shapes of first component A and second component B. In this example, first component A is a cylindrical or columnar component having an axial end 38, and second component B is a disc-shaped component having a fitting hole 40 into which axial end 38 of component A can be inserted. Concretely, in this example, an outer diameter of axial end 38 of all first component A is within a specified tolerance (e.g., between −13 μm and 0 μm with respect to 30 mm), and an inner diameter of fitting hole 40 of all second component B is within a specified tolerance (e.g., between 0 μm and +13 μm with respect to 30 mm).

For example, component assembly device 22 may be a multi-joint robot, and the multi-joint robot may be configured to grip first component A and automatically fit the gripped component into second component B which is held by a jig or another robot, etc. Concretely, axial end 38 of component A may have a taper and fitting hole 40 of second component B may also have a taper. On the other hand, component assembly device (multi-joint robot) 22 may have a mechanical floating structure or may be operated by software flexible control. In such a configuration, after components A and B are aligned by positional control of the robot within a motion accuracy of the robot, component A held by the robot is inserted into component B by the robot. Then, the floating structure or the robot holding component A controlled by the flexible control is flexibly moved along the taper, whereby the axes of components A and B precisely coincide with each other and the components are appropriately assembled.

In this regard, components A and B are surely assembled as long as the dimensions of the components are within the specified tolerance. However, when the components having the dimensions within the specified tolerance are randomly combined, component A having the outer diameter of 30 mm+0 μm and component B having the inner diameter of 30 mm+0 μm may be combined. In such a case, it is very difficult to assemble (fit) component A with component B. Moreover, in fact, the components may not be appropriately assembled due to external factors such as the friction between the components, the press force of the robot, the flexibility of the motion of the robot relative to the component, change in temperature, and vibration, etc. When such a trouble occurs during the operation of the assembly system, the operation of the system may be suspended. Therefore, in the embodiment of the present invention, such a trouble can be avoided by a process as explained below.

Figure 3:
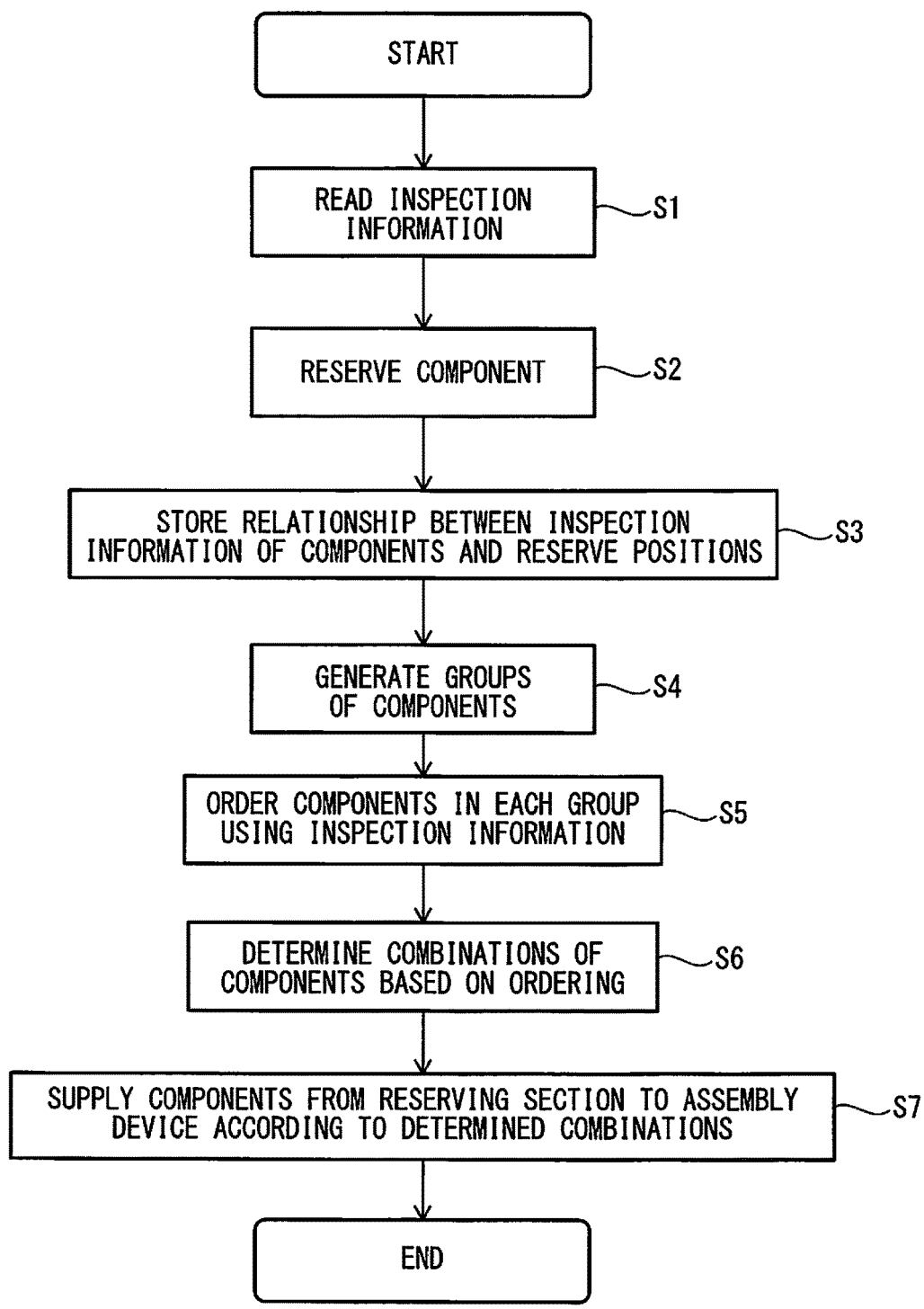
FIG. 3 is a flowchart showing an example of a procedure in the component assembly system of FIG. 1.

FIG. 3 is a flowchart showing an example of the process in component assembly system 10 according to the embodiment. First, in step S1, inspection information reading section 28 reads the first inspection information of first components A from the first inspection device, and the second inspection information of second components B from the second inspection device. After components A are manufactured by the first manufacturing device, components A are inspected by the first inspection device, and then the inspection information is added to each component A. Similarly, after components B are manufactured by the second manufacturing device, components B are inspected by the second inspection device, and then the inspection information is added to each component B. In this example, the inspection information includes a dimensional tolerance relating to easiness of assembling of the components.

The inspection information may be stored by using a 2D bar-code or an embedded memory of each component. Inspection information reading section 28 can read the inspection information by capturing the 2D bar-code by using a camera, etc., or by electrically accessing the embedded memory. Otherwise, a unique identification number (ID) may be added to each component, and the first and second inspection devices may store the inspection information associated with the ID. In this case, the inspection information associated with the ID can be transmitted to from the inspection devices to the inspection information reading section via a network, etc.

Figure 4:
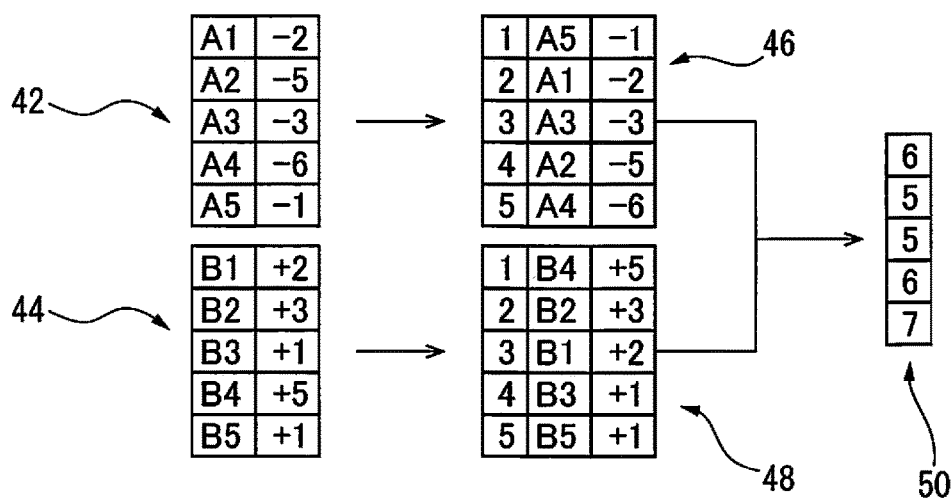
FIG. 4 is a view showing an example in which the first and second components are grouped, and the components in each group are ordered based on inspection information.

Tables 42 and 44 of FIG. 4 show examples of the inspection information of first components A1 to A5 and second components B1 to B5, respectively, which is read by inspection information reading section 28 and stored in storing section 30. For example, the stored first inspection information of components A1, A2 . . . is −2 μm, −5 μm, . . . , respectively. Similarly, the stored second inspection information of components B1, B2 . . . is +2 μm, +3 μm, . . . , respectively.

In the next step S2, the first and second components after being inspected are conveyed by component conveying device 20, and reserved (stocked) in component reserving section 24. Then, a relationship between each component, the inspection information corresponding to each component, and a reserve position of each component in component reserving section 24 is stored in storing section 30 (step S3).

In the next step S4, grouping section 32 provide one or more first group each including a predetermined number of (e.g., five) first components A and one or more second group including the predetermined number of (e.g., five) second components B. Concretely, an appropriate number "n" is determined, and then, the inspection information of first components A1 to An and second components B1 to Bn is read. In controller 26, one or more group of the first components and one or more group of the second components are generated. For example, the generated first groups includes a group of A1 to A5, a group of A6 to A10, . . . , a group of A(n−4) to An, and the generated second groups includes a group of B1 to B5, a group of B6 to B10, . . . , a group of B(n−4) to Bn.

As a method for generating the groups of the components, after reading the given "n" components, the "n" components may be divided into the groups, as explained below. Alternatively, when the components are sequentially supplied, a number of components to be included in one group may be predetermined (for example, "m" (=five) components are to be included in one group), and then "m" components may be generated as one group every time when the number of supplied components reaches "m." In addition, as the number of the components included in one group is increased, dispersion of easiness of assembling can be reduced, whereas the number of the components to be reserved in component reserving section 24 is increased. Therefore, it is preferable that an appropriate number be predetermined as the number of the components to be included in one group, based on specifications of the system, etc.

In the above example, although the number of components A included in each first group is the same (five in this case), the number of components A included in each first group may be different (for example, one group may include four components A1 to A4, and the other group may include six components A6 to A10, etc.). In this case, at least one of the second groups includes the same number of components as each first group (i.e., the second groups includes at least one group including four components B, and at least one group including six components B).

In the next step S5, combination determining section 34 determines an order of the components in each of the first and second groups by using the inspection information, and determines the combinations each including the first component in the first group and the second component in the second group, based on the determined order (step S6). In the example of FIG. 4, first components A1 to A5 are sorted in descending order of the outer diameter of the axial end as indicated by a table 46, and similarly, second components B1 to B5 are sorted in descending order of the inner diameter of the fitting hole as indicated by a table 48. As a result, one of the first and second components (in this case, the first components) are sorted in descending order of the difficulty in assembling, and the other of the first and second components (in this case, the second components) are sorted in descending order of the easiness in assembling.

Therefore, the first and second components having the same order are respectively selected and combined, and the result the selection and combination is transmitted to component conveying device 20 via supply destination commanding section 36. Component conveying device 20 conveys and supplies the first and second components corresponding to the selected combination (e.g., components A5 and B4) from component reserving section 24 to assembly device 22, with reference to the reserve positions of the components based on the relationship stored in storing section 30 (step S7). In addition, in this embodiment, the process of steps S1 to S7 may be automatically executed.

Due to the above process, the dispersion of a gap between the first and second components when assembling them is minimized as indicated by a table 50, and thus the dispersion of the easiness of assembling is minimized. Therefore, in the embodiment, in comparison to a case that the component is randomly selected from each group and the selected components are combined, there is an extremely low probability of occurring of a combination where it is difficult or impossible to combine the selected components, whereby the occurrence of the momentary stoppage of the system can be reduced or eliminated.

Figure 5:
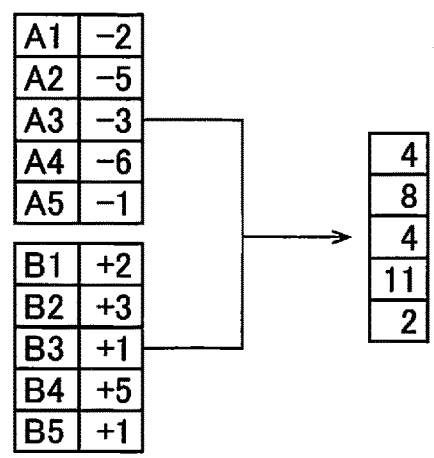
FIG. 5 is a view showing a comparative example of FIG. 4, in which the first and second components are grouped, but the components in each group are not ordered based on the inspection information.

FIG. 5 shows a comparative example of FIG. 4, in which the components are combined in a given order, without ordering the components based on the dimension, etc. of each component. In the example of FIG. 5, the dispersion of the gap between the first and second components becomes relatively large. For example, components A4 and B4 can be easily fitted with each other, whereas it is very difficult to fit components A5 and B5 with each other. On the other hand, in the embodiment, the probability of occurrence of the worst combination in view of the easiness of fitting, such as components A5 and B5, can be significantly reduced.

In the example with reference to FIG. 4, the components are ordered in each group based on the easiness of assembling, whereas the present invention is not limited as such.

For example, the first components in the first group may be ordered with respect to a dimensional error of assembled first and second components, and the second components in the second group may be ordered with respect to the dimensional error of the assembled first and second components, and the combination of the first and second components may be determined based on the ordering of the first components and the ordering of the second components so that dispersion of the dimensional error of the assembled first and second components. For example, it can be considered that FIG. 4 indicates the obtained combinations as a result of ordering the components by which the gaps between the assembled components are equalized between the combinations as possible. By virtue of this, backlashes of the assembled components (or the products) can be equalized, i.e., the qualities of the products can be equalized.

Another example of the process by combination determining section 34, all of the combinations of the first components in the first group and the second components in the second group may be evaluated by using the first and second inspection information, so that the combination of the first and second components can be determined based on the evaluation. For example, in the example of FIG. 4, with respect to all combinations of first components A1 to A5 and second components B1 to B5 (i.e., twenty-five combinations), the dispersion of the gaps between the components may be calculated similarly to table 50, and an arithmetic process may be executed so as to search and select the combination in which the dispersion of the gaps is minimized. Such a process also has an effect similar to the effect obtained by the case in which the combination of the components is determined after ordering the components in each group.

In the example of FIG. 4, the first group including components A1 to A5 and the second group including components B1 to B5 are combined. However, if the dispersion of the easiness of assembling or the dimensional error between the combinations is not sufficiently minimized or equalized, the other groups including the same number of components (e.g., the first group including components A1 to A5 and the second group including components B6 to B10) may be combined, and the similar process may be executed.

According to the present invention, the first and second components configured to be assembled with each other are respectively grouped, and the first component and second component to be assembled are determined or selected from the first and second groups, respectively, based on the inspection information of each component. Therefore, the components in one group can be combined with the components of the other group without excess or shortage, and the combinations of the components can be optimized. Such optimization cannot be carried out by handling each component individually.

While the invention has been described with reference to specific embodiments chosen for the purpose of illustration, it should be apparent that numerous modifications could be made thereto, by one skilled in the art, without departing from the basic concept and scope of the invention.

The invention claimed is:

1. A component assembly system, comprising:
   a component reserving device configured to reserve each of a plurality of first components and a plurality of second components;
   a controller configured to
      read first inspection information regarding assembling and associated with each of the plurality of first components each having a dimension within a specified tolerance, read second inspection information regarding assembling and associated with each of the plurality of second components each having a dimension within a specified tolerance and being configured to be assembled to each of the first components, store a relationship between each component among the first and second components, the inspection information of said each component, and a reserve position of said each component in the component reserving device, provide a plurality of first groups each including a predetermined number of the first components, and a plurality of second groups each including the same predetermined number of the second components, order the first components in each of the first groups based on the first inspection information, order the second components in each of the second groups based on the second inspection information, and determine a combination of one first component in each first group and one second component in each second group on one-to-one correspondence, based on the ordering of the first components and the ordering of the second components; and a component conveying device configured to convey the first and second components corresponding to the determined combination from the component reserving device to an assembly device, by using the relationship stored in the controller.

2. The component assembly system as set forth in claim 1, wherein the controller is configured to order the first components in each of the first groups with respect to easiness of assembling by using the first inspection information, order the second components in each of the second groups with respect to easiness of assembling by using the second inspection information, and determine the combination of the first and second components based on the ordering of the first components and the ordering of the second components so that dispersion of values representing the easiness of assembling between each combination is minimized.

3. The component assembly system as set forth in claim 1, wherein the controller is configured to order the first components in each of the first groups with respect to a dimensional error of assembled first and second components, order the second components in each of the second groups with respect to the dimensional error of the assembled first and second components, and determine the combination of the first and second components based on the ordering of the first components and the ordering of the second components so that dispersion of the dimensional error of the assembled first and second components between each combination is minimized.

4. A component assembly method, comprising:

reserving each of a plurality of first components and a plurality of second components in a component reserving device;

reading first inspection information regarding assembling and associated with each of the plurality of first components each having a dimension within a specified tolerance;

reading second inspection information regarding assembling and associated with each of the plurality of second components each having a dimension within a specified tolerance and being configured to be assembled to each of the first components;

storing a relationship between each component among the first and second components, the inspection information of said each component, and a reserve position of said each component in the component reserving device;

providing a plurality of first groups each including a predetermined number of the first components and a plurality of second groups each including the same predetermined number of the second components;

ordering the first components in each of the first groups based on the first inspection information;

ordering the second components in each of the second groups based on the second inspection information;

determining a combination of one first component in each first group and one second component in each second group on one-to-one correspondence, based on the ordering of the first components and the ordering of the second components; and conveying the first and second components corresponding to the determined combination from the component reserving device to an assembly device, by using the stored relationship.

5. The component assembly method as set forth in claim 4, wherein said ordering the first components includes ordering the first components in each of the first groups with respect to easiness of assembling by using the first inspection information, said ordering the second components includes ordering the second components in each of the second groups with respect to easiness of assembling by using the second inspection information, and said determining includes determining the combination of the first and second components based on the ordering of the first components and the ordering of the second components so that dispersion of values representing the easiness of assembling between each combination is minimized.

6. The component assembly method as set forth in claim 4, wherein said ordering the first components includes ordering the first components in each of the first groups with respect to a dimensional error of assembled first and second components, said ordering the second components includes ordering the second components in each of the second groups with respect to the dimensional error of the assembled first and second components, and said determining includes determining the combination of the first and second components based on the ordering of the first components and the ordering of the second components so that dispersion of the dimensional error of the assembled first and second components between each combination is minimized.

* * * * *